(12) United States Patent
Mäkiranta

(10) Patent No.: US 10,807,755 B2
(45) Date of Patent: Oct. 20, 2020

(54) EMPTYING DEVICE, ASSEMBLY AND METHOD FOR EMPTYING SUCTION BAG

(71) Applicant: Serres Oy, Kauhajoki As. (FI)

(72) Inventor: Jarmo Mäkiranta, Kauhajoki (FI)

(73) Assignee: Serres Oy, Kauhajoki As., OT (FI)

( * ) Notice: Subject to any disclaimer, the term of this patent is extended or adjusted under 35 U.S.C. 154(b) by 783 days.

(21) Appl. No.: 15/322,226

(22) PCT Filed: Jun. 30, 2015

(86) PCT No.: PCT/FI2015/050479
§ 371 (c)(1),
(2) Date: Dec. 27, 2016

(87) PCT Pub. No.: WO2016/001488
PCT Pub. Date: Jan. 7, 2016

(65) Prior Publication Data
US 2017/0152069 A1    Jun. 1, 2017

(30) Foreign Application Priority Data

Jul. 3, 2014 (FI) .................................... 20145647

(51) Int. Cl.
*A61M 1/00* (2006.01)
*B65B 69/00* (2006.01)
*A61M 27/00* (2006.01)
*A61F 13/00* (2006.01)
*A61F 13/02* (2006.01)
(Continued)

(52) U.S. Cl.
CPC ....... *B65B 69/0016* (2013.01); *A61M 1/0005* (2013.01); *A61J 1/10* (2013.01)

(58) Field of Classification Search
CPC ........ A61M 1/00; A61M 13/02; A61M 27/00; A61F 13/00; A61B 17/50
See application file for complete search history.

(56) References Cited

U.S. PATENT DOCUMENTS 3,809,577 A    5/1974   Thorsson et al.
5,419,670 A    5/1995   Sommer, Jr. et al.
(Continued)

FOREIGN PATENT DOCUMENTS

DE    19750093 C1  *  12/1997
DE    19750093 C1     2/1999
(Continued)

OTHER PUBLICATIONS

PCT Written Opinion of the International Searching Authority, dated Dec. 9, 2015; 5 pages.
(Continued)

*Primary Examiner* — Tatyana Zalukaeva
*Assistant Examiner* — Ilya Y Treyger
(74) *Attorney, Agent, or Firm* — Seyfarth Shaw LLP

(57) ABSTRACT

The invention relates to a suction bag emptying device (20) comprising a container (19) for receiving a suction bag (3), the container (19) having a discharge point for discharging the contents of the suction bag. The emptying device (20) comprises means for puncturing a bag portion without making contact with the bag. The invention further relates to an assembly comprising at least one suction bag (3) and a suction bag emptying device (20), and to a method for emptying a suction bag (3).

10 Claims, 6 Drawing Sheets

(51) Int. Cl.
    *A61B 17/50*     (2006.01)
    *A61J 1/10*     (2006.01)

(56)     References Cited

U.S. PATENT DOCUMENTS

| | | |
|---|---|---|
| 5,622,471 A | 4/1997 | Sommer, Jr. et al. |
| 2012/0048080 A1 | 3/2012 | Zardini |
| 2013/0170772 A1 | 7/2013 | De With |
| 2014/0336029 A1* | 11/2014 | Mirle .................... B65D 31/12 493/267 |

FOREIGN PATENT DOCUMENTS

| | | |
|---|---|---|
| EP | 0541402 | 5/1993 |
| EP | 0713831 | 5/1996 |
| EP | 0864499 A1 | 9/1998 |
| WO | 0124846 A1 | 4/2001 |
| WO | 02067839 A1 | 9/2002 |
| WO | 2002074632 | 9/2002 |
| WO | 2010128377 A2 | 11/2010 |

OTHER PUBLICATIONS

European search report for Application No. 15815917.8, dated May 14, 2018, 5 pages.
Office Action for Finnish Application No. 20145647 dated Nov. 24, 2017, 4 pages.

* cited by examiner

EMPTYING DEVICE, ASSEMBLY AND METHOD FOR EMPTYING SUCTION BAG

CROSS REFERENCE TO RELATED APPLICATIONS

This is a National Stage application of PCT/FI2015/050479, filed Jun. 30, 2015, which claims priority to Finland Patent Application No. 20145647, filed Jul. 3, 2014, the disclosures of which are incorporated herein by reference.

BACKGROUND OF THE INVENTION

The invention relates to a suction bag emptying device comprising a container for receiving a suction bag, the container having a discharge point for discharging the contents of the suction bag.

The invention also relates to an assembly comprising at least one suction bag and a suction bag emptying device, and to a method for emptying a suction bag.

Publication U.S. Pat. No. 3,809,577 discloses a device provided with a lid and scissor- or knife-like members that cut open the bottom of the suction bag. Suction bags are placed in the device in a basket and the lid is closed, the basket being thus pressed down towards the scissor- or knife-like members that cut open the suction bags. The closing of the lid of the device also activates a rinsing process in which the suction bags are rinsed and disinfected.

A problem with the device of the above publication is that, firstly, its structure is complicated. Secondly, it is not certain that the suction bag could be emptied completely. Thirdly, the suction bags are cut in an uncontrollable manner at the point where they are within the reach of the scissor- or knife-like members.

BRIEF DESCRIPTION OF THE INVENTION

An emptying device according to the invention provides an improvement over the aforementioned problems. The emptying device according to the invention is characterized in that the emptying device comprises means for puncturing a bag portion without making contact with the bag.

The structure of the emptying device is simple, making the device reliable and maintenance-free. The suction bag is sure to empty. The contents of the bag are emptied in a controlled manner substantially through the same point in a lower part of the bag, leaving no pockets containing body fluids in the suction bag. Savings in waste costs are significant when all that needs to be disposed of is the empty suction bag, which is taken to incineration, for example, for disposal. If an emptying device provided with a rinsing possibility is used, the rinsing runs through the entire bag.

A further advantage of the emptying device according to the invention is that the device may be used for emptying suction bags of different lengths. The device may also be constructed such that it contains no sharp parts to come into contact with by a person emptying the suction bag. The person emptying the suction bag is also well protected against possible splatter because the suction bag tightens against the emptying device so that the contents of the suction bag are not allowed to splash upwards.

The emptying device is particularly suitable for suction bags, but the emptying device may also be used for other bags containing body fluids. Suction bags are used in hospitals or other facilities performing medical operations, such as surgery. The emptying device according to the invention may be used for instance for a suction bag such as the one described below:

The suction bag usually comprises a bag portion and a lid fixedly attached to the bag portion. The bag portion is made of a flexible plastic material, such as polyethylene. The bag portion is formed of a tubular plastic film. One end of the tubular plastic film is closed by sealing the edges of the plastic film together, while at its other end the tubular plastic film is fixedly attached to the lid. Also the lid is made of a polyolefin plastic material, such as polyethylene or polypropylene, but it is stiffer than the bag portion. The lid is a substantially uniform piece. The lid has a patient fitting to be coupled to a hose delivering fluid from the patient to the suction bag. The lid is also provided with a channel for transmitting negative pressure, and a filter for preventing impurities from entering the suction system. Usually, the filter is fastened to an inner surface side of the suction bag lid, but it may also be located elsewhere in connection with the aforementioned channel.

The suction bag is used with a collection reservoir whose one end is open, and together they form a suction bag arrangement. The bag portion of the suction bag is placed inside the collection reservoir, the suction bag lid closing the collection reservoir. The collection reservoir is provided with a fitting that has a flow connection to a source of negative pressure for generating a negative pressure between an inner surface of the collection reservoir and an outer surface of the suction bag. The lid is provided with a channel for transmitting the negative pressure from a space between the inner surface of the collection reservoir and the lid to an inner part of the suction bag.

The details of the suction bag suitable to be handled in the emptying device may differ from those disclosed above. Usually, however, the bag has a flexible bag portion and a stiffer lid fixedly attached thereto.

In the following, the structure and operation of the bag emptying device will be described. The emptying device is described in the position in which it is used.

The bag emptying device comprises a container for receiving a bag. The bag may be placed in the container without support, or it may be placed in a holder provided in the container. At its simplest, the holder is a rim of the container whereon a rim of the suction bag lid settles. The holder may also be a shoulder or another arrangement provided in the container and suitable for suspending the bag. The shoulder is formed of an annular piece at the mouth of the container, an inner rim of the piece bordering on an outer wall of a jacket of the emptying device. Further, at least one suction bag suspension device may be provided on the suction bag lid or in connection therewith, a corresponding holder being provided in the emptying device. The emptying device may be provided with a jacket for supporting the suction bag laterally. The jacket may form an inner wall of the container jacket particularly when the emptying device is to be used for handling only one bag at a time. When the emptying device has a plural number of positions for bags to be emptied, a separate jacket is provided for each position. The rim of the suction bag lid rests on the shoulder or the like, and the bag portion of the bag hangs downward. The container is also provided with a discharge point for discharging the contents of the suction bag.

After the suction bag has been placed in the container, the means for puncturing a bag portion without making contact with the bag are started or they start automatically.

According to a first embodiment, the means for puncturing a bag portion without making contact with the bag comprise an arrangement for conveying negative pressure to the emptying device. A suitable point in a lower part of the emptying device is provided with a negative pressure suction, whereby the bag portion of the suction bag is punctured and the bag empties.

According to a second embodiment, the means for puncturing a bag portion without making contact with the bag comprise an electric resistance. A suitable point in the lower part of the emptying device is provided with an electric resistance to puncture the bag portion by melting or burning.

According to a third embodiment, the means for puncturing a bag portion comprise a device that cuts without contact. The device that cuts without contact may be a laser cutter, for instance.

The emptying device may have a lid and it may be provided with means for puncturing the lid of the suction bag and for conveying pressurized liquid or gas into the bag to be emptied. The aforementioned means may also be separate from the lid. Liquid or gas is supplied to the bag for rinsing and/or disinfecting the bag.

The means for puncturing the lid of the bag and for conveying pressurized liquid or gas into the suction bag to be emptied may be implemented in many ways. The means may be for instance a hollow cone with an obtuse end, or a hollow cylinder provided with a cutting edge, or a hollow cone with a fixed, spiky end. The aforementioned means enable the lid of the suction bag to be punctured. The means have openings through which the liquid or gas is allowed to flow after the lid of the suction bag has been punctured. Naturally, the above are only examples of how the means in question may be implemented. In practice, the means for puncturing the lid of the bag and for conveying pressurized liquid or gas into the bag to be emptied may be one or more parts, but these means enable two functions to take place: puncturing the lid of the bag and conveying pressurized liquid or gas into the bag. Naturally, an outer surface of the lid is provided with a connector/connectors for connecting the emptying device to a source of liquid or gas, the connectors, in turn, being connected to the means for puncturing the lid of the bag and for conveying pressurized liquid or gas into the bag to be emptied.

The means for puncturing a bag portion without making contact with the bag are started or they start automatically. According to a first embodiment, a negative pressure suction is conveyed to the emptying device to puncture the bag portion in a controlled manner at a predetermined location.

According to a second embodiment, the emptying device is provided with an electric resistance to puncture the bag portion by melting or burning.

According to a third embodiment, the emptying device is provided with a device that cuts without contact. The device that cuts without contact may be a laser cutter, for instance.

The means for conveying pressurized liquid or gas into the bag to be emptied are arranged to be activated when the bag portion has been punctured and the lid has been punctured. In other words, after the channel/channels delivering liquid or gas has/have penetrated the lid of the suction bag, the liquid or gas starts flowing into the suction bag.

The source of pressurized gas or liquid may be a water distribution system or a pressurized air network, for instance. It is also possible to feed disinfectants or sterilizing agents from the source of pressurized gas or liquid. In an emptying device provided with a lid, the opening of the source of pressurized gas or liquid may be combined with the closing of the lid, in which case the gas or liquid starts automatically flowing into the bag to be emptied. At its simplest, the opening of the source of gas or liquid may take place by opening it manually, by turning on a water tap, for instance.

After the bag has been punctured without contact, the contents of the bag flow out of the bag. The container is provided with a discharge point through which the contents of the bag are arranged to be discharged. It is also possible that fluid being discharged through the discharge point is conveyed to a closed container for further processing, or fluid being discharged through the discharge point is sterilized before being discharged to the drain.

The flow of gas or liquid rinses the inside of the bag. The bag is then sure to empty, and the rinsing ensures that the inside of the bag is cleaned. When a puncture is made in the lower part of the suction bag in a controlled manner, the pressurized gas or liquid flows through the entire bag, in which case no pockets are formed in the bag that might contain residue of fluids collected from the body.

When the rinsing has been going on for a necessary period of time, the gas or liquid flow is closed down or the flow closes down automatically for instance by opening the lid of the emptying device or at the expiry of a pre-timed rinsing time. The rinsed bag may then be removed from the emptying device and put to waste.

The emptying device may be constructed in many different ways. The emptying device may be a device intended for handling only one bag at a time, as shown in FIGS. 3a, 3b, 4a and 4b below. When the emptying device has one position for a bag to be emptied, the jacket supporting the bag laterally may be the inner wall of the container. The emptying device may have a plurality of positions for placing a plurality of suction bags in the device at a time. When the emptying device has a plurality of positions for suction bags to be emptied, the jacket supporting the bag laterally is a separate structural part provided inside the container. No jacket is necessary, and it is advantageous usually in connection with the use of negative pressure.

The device may have a uniform lid, which may be provided with a plurality of means for puncturing the lid of the suction bag and for conveying pressurized gas or liquid into the suction bag to be emptied. In such a case, by closing the lid of the emptying device, it is possible to puncture the lids of a plurality of bags and start simultaneous rinsing of the plurality of bags. The emptying device may also have a plurality of positions for placing a plurality of bags in the device at a time such that the emptying device has for each bag a separate lid which is provided with means for puncturing the lid of the bag and for conveying pressurized gas or liquid into the bag to be emptied. Such an arrangement enables a plurality of bags to be rinsed simultaneously such that when a first bag is in its place, the lid may be closed and rinsing may be started immediately while at the same time it is possible to continue filling the rest of the positions.

It is advantageous if the suction bags and the emptying device are used as an assembly compatible with one another. In other words, the emptying device is dimensioned to correspond to a specific suction bag/specific suction bags. This enables the advantages of the emptying device to become even more apparent.

BRIEF DESCRIPTION OF THE FIGURES

The invention is now described in closer detail in connection with preferred embodiments and with reference to the accompanying drawings, in which.

DETAILED DESCRIPTION OF THE INVENTION

Figure 1:
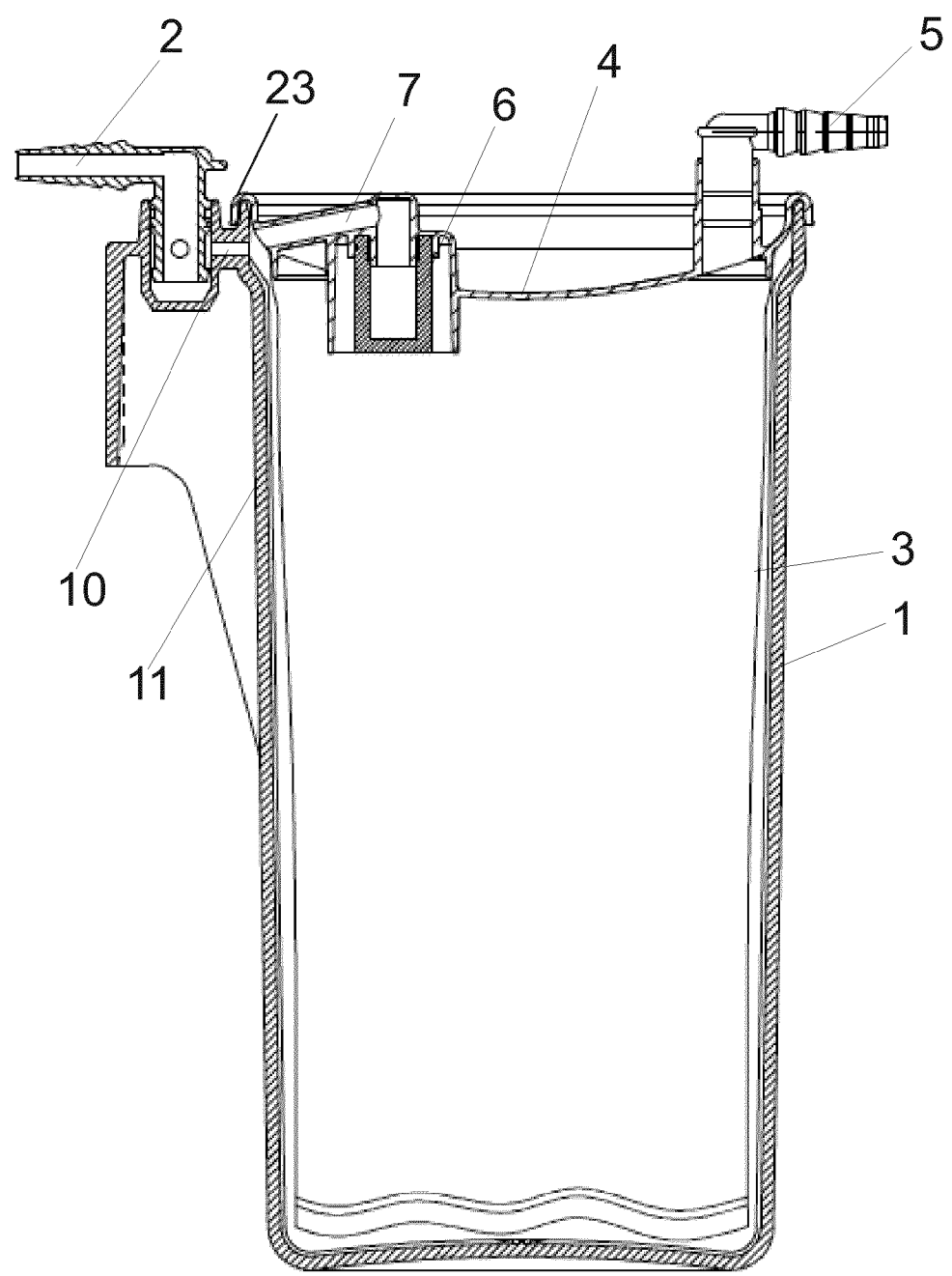
FIG. 1 is a side view showing a suction bag arrangement.
Figure 2:
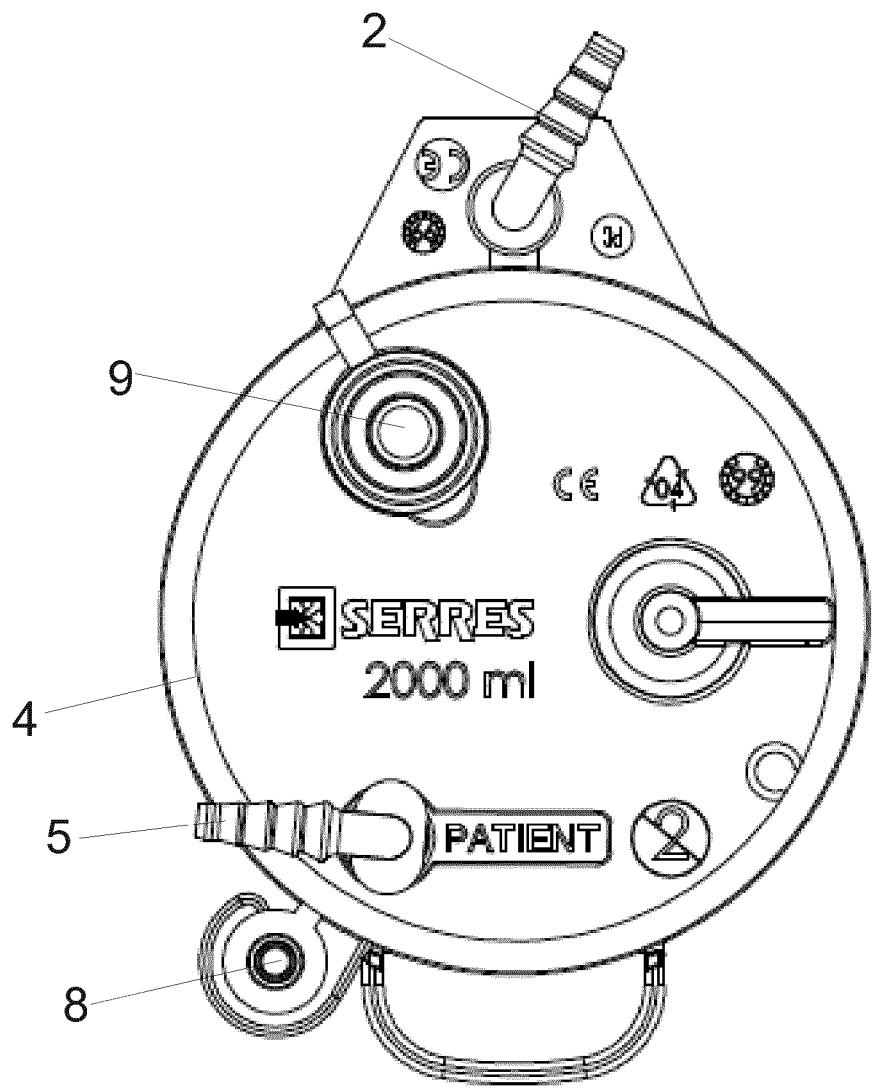
FIG. 2 is a top view showing the suction bag arrangement according to FIG. 1.

FIGS. 1 and 2 describe first the structure and operation of a suction bag 3. The suction bag according to FIGS. 1 and 2 is an example of a suction bag suitable to be emptied by an emptying device according to the invention.

According to what is shown in FIG. 1, the suction bag arrangement comprises a collection reservoir 1 whose one end is open, a suction bag 3 arrangeable in the collection reservoir 1 and comprising a flexible bag portion fixedly fastened to a lid 4. The collection reservoir 1 is provided with a fitting 2, which has a flow connection to a source of negative pressure, and a channel 10 for generating a negative pressure in a region 11 between the inner surface of the collection reservoir 1 and the outer surface of the suction bag 3. The lid 4 is provided with a patient fitting 5 for coupling a patient hose to an inner part of the suction bag 3, and the lid 4 has a channel 7 for transmitting negative pressure from a space between the inner surface of the collection reservoir 1 and the lid 4 to the inner part of the suction bag 3, and a filter 6 for preventing impurities from entering the suction system. The filter 6 is fastened to an inner surface side of lid of the suction bag 3, and the lid 4 is a uniform piece.

FIG. 2 is a top view showing the suction bag arrangement. In addition to the parts described in FIG. 1, FIG. 2 shows a plug 8 integrated in the lid 4 to enable the patient fitting 5 to be closed after use, and a connector 9 to be used for connecting the suction bag arrangements in series as well as for sampling and for manual emptying. The connector 9 may also be used for dispensing a solidifying agent.

FIGS. 3a, 3b, 4a and 4b show an emptying device 20 whose container 19 is provided with a suction bag 3 suspended from rims 23 of its lid 4. Preferably but not, however, necessarily, a jacket 12 of the emptying device 20 resides close to a surface of a bag portion of the suction bag 3. The emptying device 20 also includes an intermediate container 13. A valve 16 is provided between the intermediate container 13 and the container 19. The intermediate container 13 has a channel 15 for conveying negative pressure into the intermediate container 13, and a channel 14 for discharging the contents of the suction bag. The channel 15 is provided with a valve 17 while the channel 14 is provided with a valve 18.

Figure 3A:
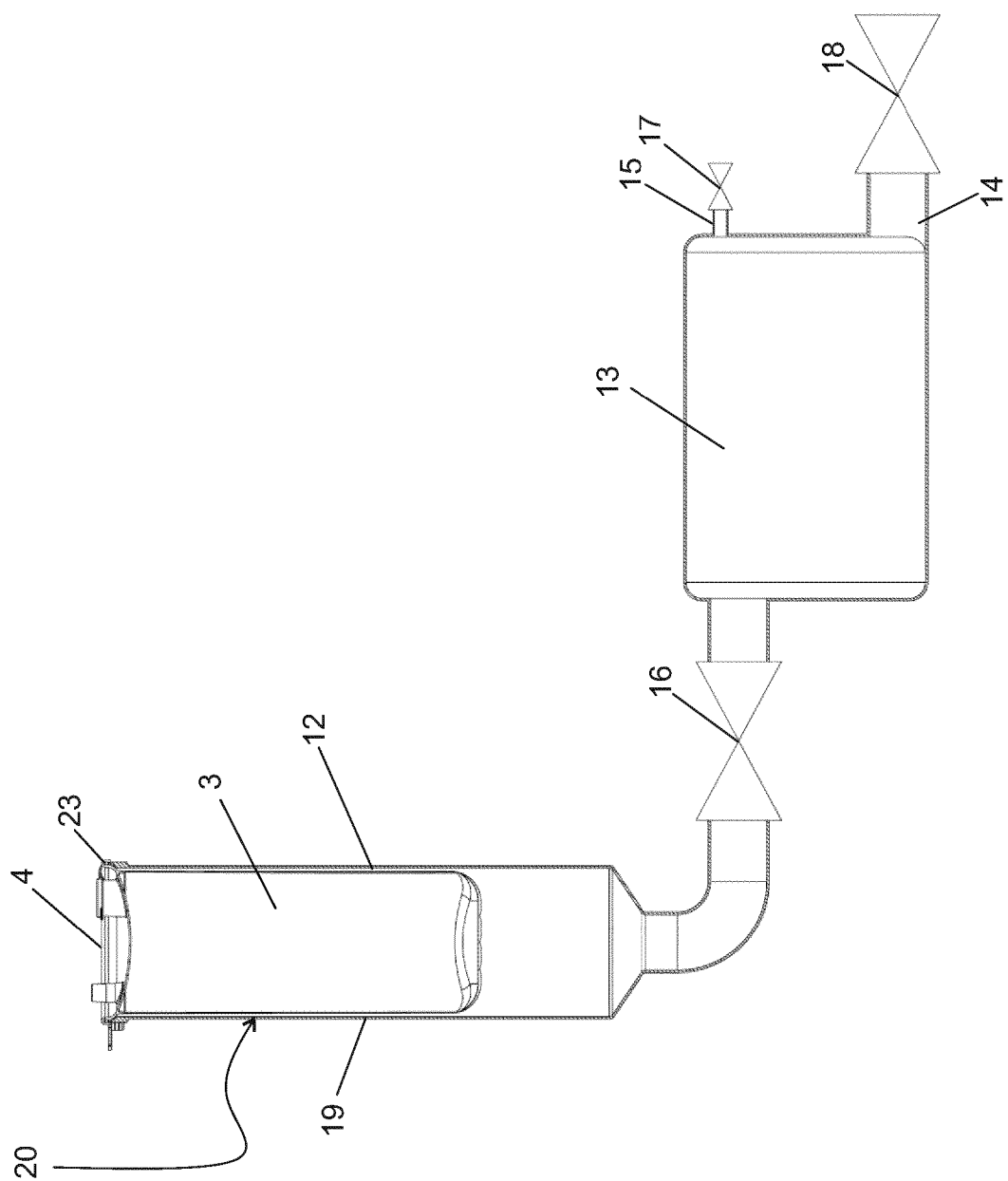
FIGS. 3a, 3b, 4a and 4b are cross sections of an emptying device according to the invention.
Figure 3B:
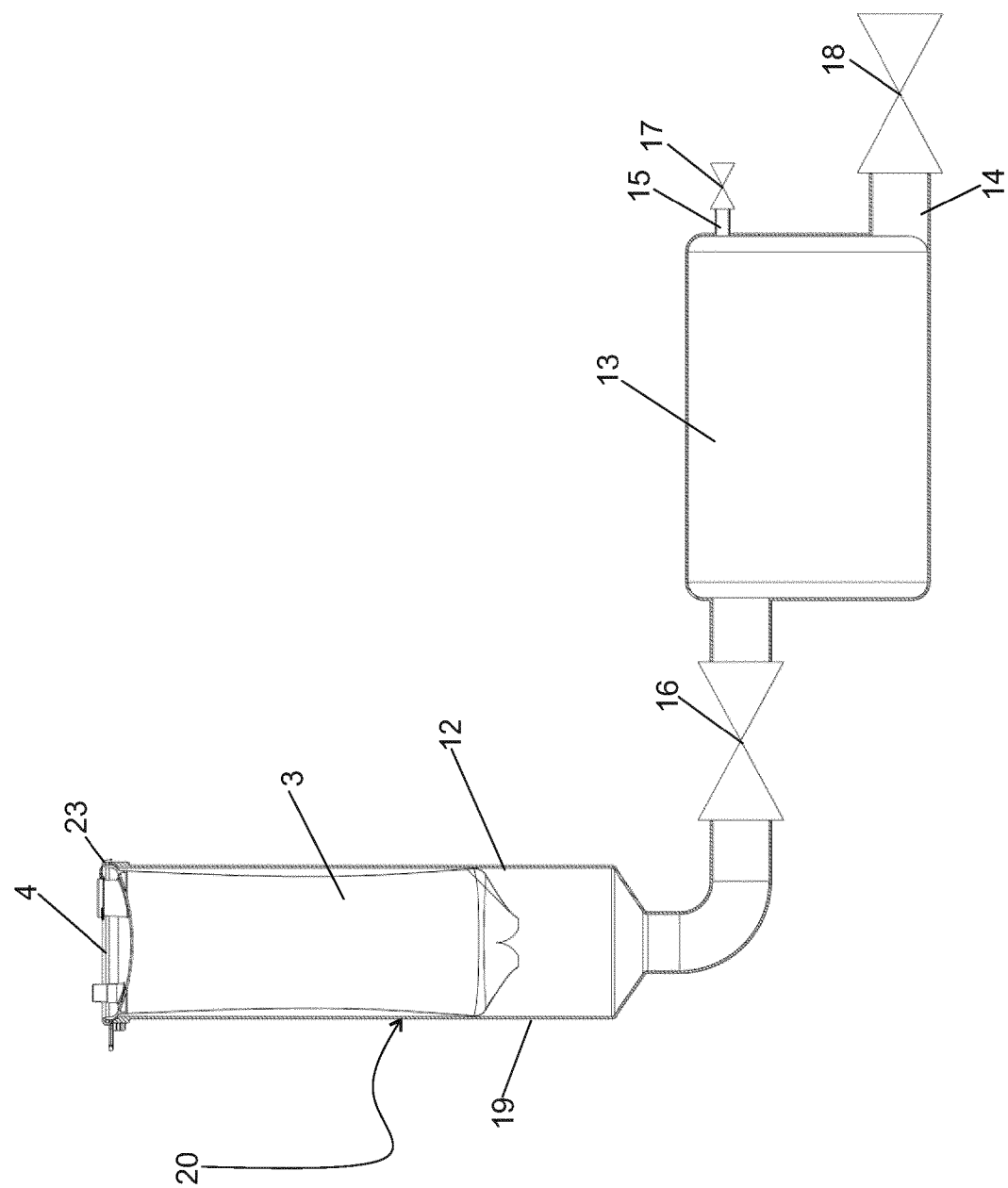

FIG. 3a shows an initial situation of emptying of the suction bag 3. The valve 18 is closed and the valve 17 is opened for conveying negative pressure first to the intermediate container 13 and, after opening the valve 16, to the container 19. The lid 4 closes the mouth of the container 19 so that in the container 19 a negative pressure suction is formed which starts stretching the bottom of the suction bag 3 such that eventually the bottom is ruptured and the contents of the suction bag 3 flow into the intermediate container 13. FIG. 3b shows a situation wherein the suction bag 3 has already ruptured. The valves 16 and 17 are closed and the valve 18 is opened, enabling the contents of the suction bag to be discharged from the intermediate container 13 along the channel 14. It is also possible that the container 19, the intermediate container 13, the suction bag 3 and the contents of the suction bag are disinfected by steam supplied through the valves 17 and 16. The intermediate container 13 may also be a steam generator for carrying out the aforementioned procedure.

Figure 4A:
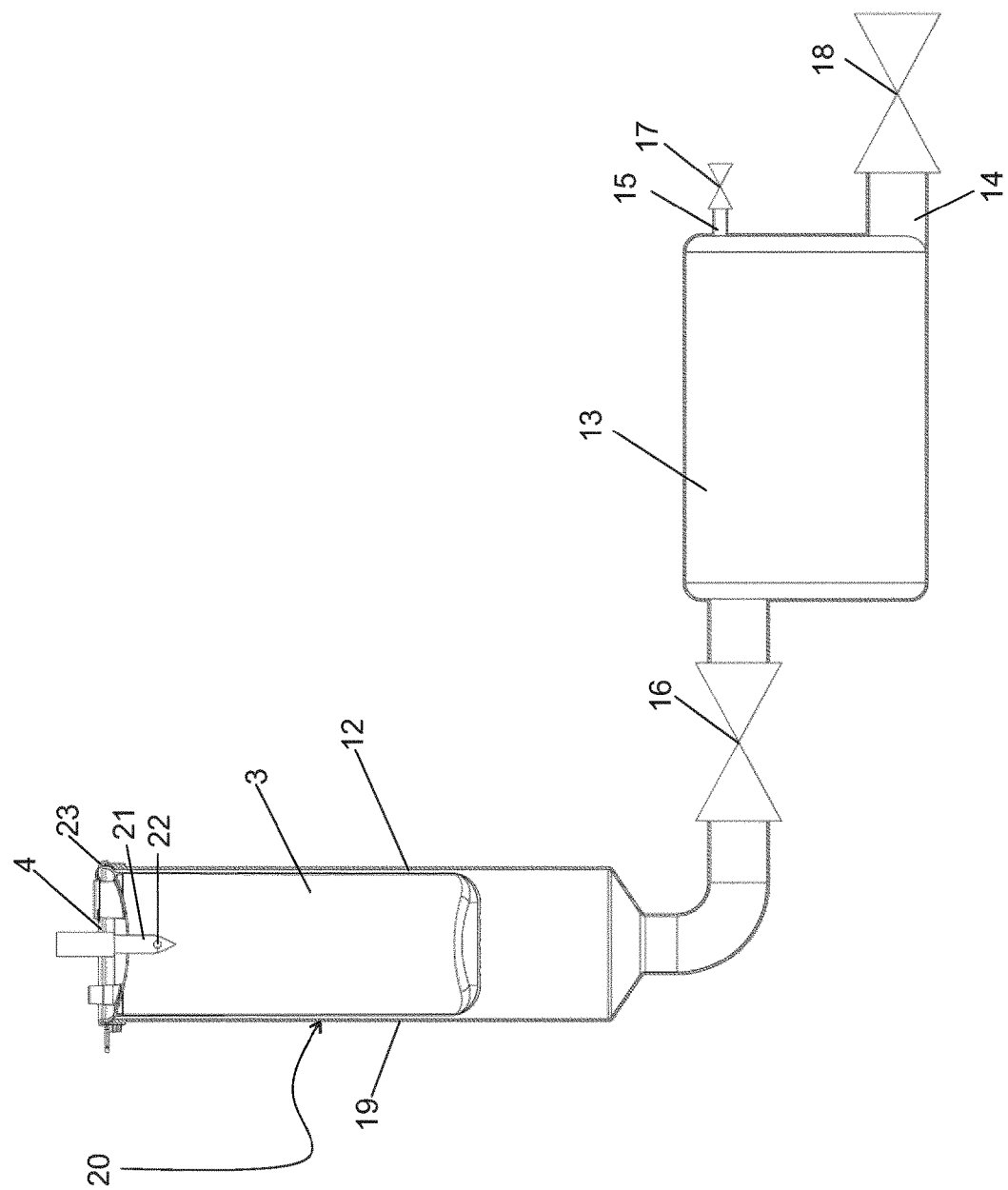
Figure 4B:
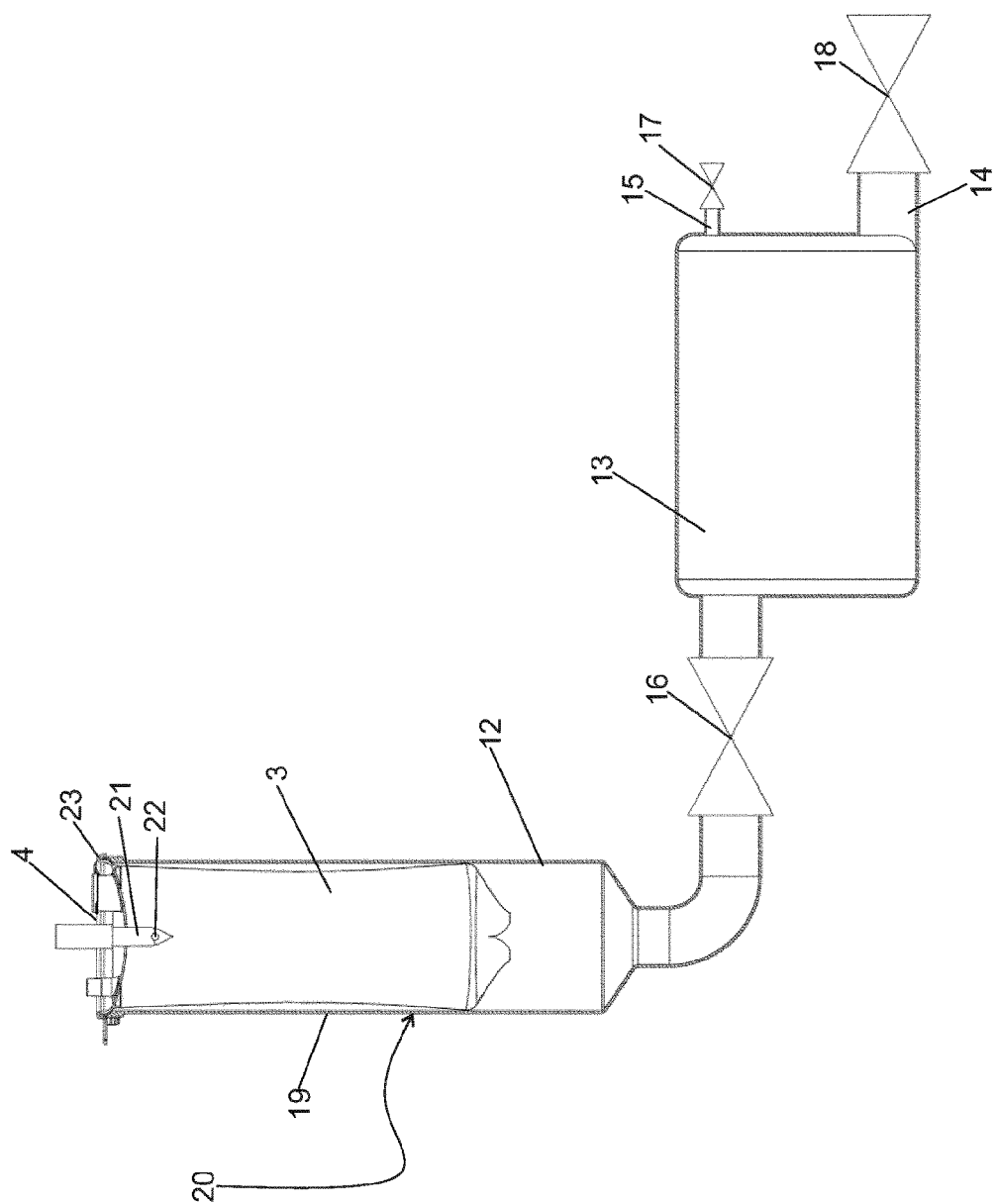

FIG. 4a shows a situation before the suction bag 3 is ruptured while FIG. 4b shows a situation after the suction bag 3 has ruptured. A difference between the situation shown in FIGS. 4a and 4b and that in FIGS. 3a and 3b is that through the lid 4 of the suction bag 3 is pressed a hollow cone 21 provided with at least one opening 22 through which liquid or gas flows into the suction bag 3 for rinsing and/or disinfecting the suction bag. The cone 21 is in connection with a source of liquid or gas, and it may be, but is not necessarily, fastened to the lid possibly provided in the emptying device 20.

It is apparent to one skilled in the art that as technology advances, the basic idea of the invention may be implemented in many different ways. The invention and its embodiments are thus not restricted to the above-described examples but may vary within the scope of the claims.

The invention claimed is:

1. A suction bag emptying device adapted to puncture a suction bag without making contact therewith, comprising:
 a container adapted to receive the suction bag, the container includes a discharge point adapted to discharge contents of the suction bag; and
 an intermediate container adapted to receive contents of the suction bag, the intermediate container includes:
  a first channel adapted to convey negative pressure into the emptying device, wherein the first channel includes a first valve; and
  a second channel including a second valve and adapted to discharge contents of the suction bag.

2. The suction bag emptying device of claim 1, further comprising a jacket adapted to support the suction bag laterally.

3. The suction bag emptying device of claim 2, wherein the jacket is an inner wall of the container.

4. The suction bag emptying device of claim 1, further comprising a plurality of positions respectively for a plurality of suction bags to be emptied.

5. An assembly comprising:
 a suction bag and a suction bag emptying device adapted to puncture the suction bag without making contact therewith,
 wherein the suction bag includes a lid and a bag portion fixedly fastened to the lid, and
 wherein the suction bag emptying device includes:
  a container having a discharge point adapted to discharge contents of the suction bag, and
  an intermediate container adapted to receive contents of the suction bag, wherein the intermediate container includes:
   a first channel adapted to convey negative pressure into the suction bag emptying device, wherein the first channel includes a first valve; and
   a second channel having a second valve and adapted to discharge contents of the suction bag.

6. The assembly of claim 5, wherein the suction bag emptying device has one position for the suction bag to be emptied.

7. The assembly of claim 5, wherein the suction bag emptying device has a plurality of positions respectively for a plurality of suction bags to be emptied.

8. A method for emptying a suction bag comprising:
 selecting an emptying device adapted to puncture the suction bag without making contact therewith, the emptying device including a container having a discharge point adapted to discharge contents of the suction bag and an intermediate container adapted to receive contents of the suction bag, the intermediate container includes a first channel including a first valve adapted to convey negative pressure into the emptying device, and a second channel adapted to discharge contents of the suction bag and including a second valve;
 placing the suction bag in the container;
 opening the first valve to convey negative pressure into the emptying device, thereby causing the suction bag to puncture;
 closing the first valve;
 opening the second valve; and
 removing the suction bag from the emptying device.

9. The method of claim 8, wherein the emptying device includes a plurality of positions respectively for a plurality of suction bags, and further comprising respectively placing the plurality of suction bags on the plurality of positions of the emptying device, and starting the emptying device without making contact with the plurality of suction bags.

10. The method of claim 8, wherein the emptying device includes a plurality of positions respectively for a plurality of suction bags, and further comprising repeating the following procedure at each position of the plurality of positions:

placing in the emptying device one of the suction bags of the plurality of suction bags; and starting the emptying device without making contact with the one suction bag.

\* \* \* \* \*